US010823730B2

(12) United States Patent
Nonaka et al.

(10) Patent No.: US 10,823,730 B2
(45) Date of Patent: Nov. 3, 2020

(54) METHOD AND KIT FOR IMMUNOLOGICAL DETECTION OF *MYCOBACTERIUM TUBERCULOSIS*

(71) Applicants: BL CO., LTD., Numazu-shi, Shizuoka (JP); ARNOTECH CO., LTD., Numzau-shi, Shizuoka (JP)

(72) Inventors: Urao Nonaka, Numazu (JP); Toshiyuki Kitagawa, Numazu (JP)

(73) Assignee: TAUNS CO., LTD., Shizuoka (JP)

( * ) Notice: Subject to any disclaimer, the term of this patent is extended or adjusted under 35 U.S.C. 154(b) by 0 days.

(21) Appl. No.: 14/390,706

(22) PCT Filed: Apr. 4, 2013

(86) PCT No.: PCT/JP2013/060301
§ 371 (c)(1),
(2) Date: Oct. 3, 2014

(87) PCT Pub. No.: WO2013/151122
PCT Pub. Date: Oct. 10, 2013

(65) Prior Publication Data
US 2015/0064729 A1    Mar. 5, 2015

(30) Foreign Application Priority Data

Apr. 5, 2012 (JP) .................. 2012-086566

(51) Int. Cl.
| A61K 39/00 | (2006.01) |
| A61K 39/04 | (2006.01) |
| C07K 2/00 | (2006.01) |
| G01N 33/569 | (2006.01) |
| G01N 33/543 | (2006.01) |

(52) U.S. Cl.
CPC ....... *G01N 33/5695* (2013.01); *G01N 33/543* (2013.01)

(58) Field of Classification Search
CPC ........ A61K 38/02; A61K 39/00; A61K 39/04; A61K 39/395; C07K 2/00; C07K 14/195; C07K 14/35; C07K 16/00; C07K 16/12; C07K 16/1289
See application file for complete search history.

(56) References Cited

U.S. PATENT DOCUMENTS

| 8,541,179 B2 * | 9/2013 | Namba ............. 435/7.1 |
| 2010/0285506 A1 * | 11/2010 | Namba ............. 435/7.32 |
| 2016/0238599 A1 | 8/2016 | Nonaka et al. | |

FOREIGN PATENT DOCUMENTS

| CN | 104246505 B | 8/2016 | |
| EP | 0273333 A2 | 7/1988 | |
| EP | 2226635 A1 * | 9/2010 | ......... C07K 16/1289 |
| JP | H07-110332 A | 4/1995 | |
| JP | H11108931 A | 4/1999 | |
| JP | 2002-062299 A | 2/2002 | |
| JP | 2004-166564 A | 6/2004 | |
| JP | 2006-184295 A | 7/2006 | |
| JP | 2006-234627 A | 9/2006 | |
| WO | 9734149 A1 | 9/1997 | |
| WO | 2009/084481 A1 | 7/2009 | |

OTHER PUBLICATIONS

Bekmurzayeva, A., et al. Tuberculosis, vol. 91, No. 4, pp. 381-388, Jul. 2013.*
Oettinger, T., et al. Infection and Immunity, vol. 62, No. 5, pp. 2058-2064, May 1994.*
Yin, X., et al. Journal of Infection, vol. 67, No. 5, pp. 369-377, Nov. 2013.*
International Search Report dated May 28, 2013, issued in International Application PCT/JP2013/060301.
International Preliminary Report on Patentability dated Oct. 7, 2014, corresponding with International Application PCT/JP2013/060301.
Chinese Office Action and Translation issued against Chinese Patent Application No. 201380018968.0 dated Jun. 1, 2015.
Office Action dated Jul. 12, 2016, for Russian Application No. 2014144283/15(071428), together with English language translation thereof.
Extended European Search Report dated Nov. 4, 2015 in European Application No. 13772467.
Office Action dated Sep. 5, 2016, for Chinese Application No. 201610009079.3.
Office Action dated Mar. 7, 2017 issued in counterpart JP application.
State Intellectual Property Office of P.R. China, Office Action (with translation) dated Mar. 16, 2017 is Chinese Appln. 201610245191.7.
Minutes of interview issued by Russian Patent Office on Oct. 13, 2017 in Russian application 201444283.
Minutes issued by Russian Patent Office on Jun. 15, 2017 in Russian application 201444283.

(Continued)

*Primary Examiner* — Rodney P Swartz
(74) *Attorney, Agent, or Firm* — Fitch, Even, Tabin & Flannery, LLP

(57) ABSTRACT

Definitive diagnosis and early start of treatment cannot be made for tuberculosis since conventional methods for detecting a *Mycobacterium tuberculosis* complex require a long time plus enormous labor and expense. Because detection is difficult to perform directly from a biological sample, if the biological sample contains no or a very small amount of MPT64, there is a risk infection with the *Mycobacterium tuberculosis* complex will be missed. The present method and a kit address these long-standing needs by more rapidly and conveniently detecting a *Mycobacterium tuberculosis* complex, without culturing a biological sample containing the *Mycobacterium tuberculosis* complex, in which a biological sample is subjected to a heat-treatment so as to extracellularly secrete a *Mycobacterium tuberculosis* complex-specific secretory protein, particularly, MPB64, and subjecting the resulting treated sample to an immunological measurement/assay.

14 Claims, 1 Drawing Sheet

(56) References Cited

OTHER PUBLICATIONS

Office Action dated May 16, 2017 issued by State Intellectual Property Office for P.R. China in PRC appln. No. 201610009079.3.
Office Action issued in EP 13772467.0, dated Nov. 9, 2017.
European Search Report dated Oct. 7, 2016, for European Application No. 16166865.2.
EPO Communication dated Jul. 18, 2018 in EP13772647.0.
Office Action issued in EP 15166865.2, dated Nov. 28, 2017.
EPO Communication issued in EP 13772467.0, dated Mar. 22, 2018.
EPO Communication dated Jul. 20, 2018 in EP16166865.2.
Office Action—First Examination Report—(India) dated Jun. 25, 2019 against IN Application No. 8246/DELNP/2014.
Abe et al., Journal of Clinical Microbiology, 37(11):3683-3697 (1999).
Mufasa et al., Modern Pathology, 19:1601-1614 (2006).
Office Action issued against corresponding BR Patent Application No. BR112014024574-6, English translation submitted herewith (7 pages).
Office Action issued against corresponding EP Patent Application No. 19150248.3 (6 pages).

\* cited by examiner

METHOD AND KIT FOR IMMUNOLOGICAL DETECTION OF *MYCOBACTERIUM TUBERCULOSIS*

CROSS-REFERENCE TO RELATED APPLICATIONS

This Application is a U.S. National Stage Application filed under 35 U.S.C. § 371 of International Application PCT/JP2013/060301, filed Apr. 4, 2013, designating the United States, which claims priority from Japanese Patent Application 2012-086566, filed Apr. 5, 2012, the complete disclosures of which are hereby incorporated herein by reference in their entirety for all purposes.

TECHNICAL FIELD

The present invention relates to a highly safe method and a kit for immunological detection of a *Mycobacterium tuberculosis* complex which can be conveniently and rapidly performed directly from a biological sample containing the *Mycobacterium tuberculosis* complex without culture operation by heat-treating the biological sample at a predetermined temperature and immunologically detecting a *Mycobacterium tuberculosis* complex-specific secretory protein thus extracellularly secreted.

BACKGROUND ART

Tuberculosis is currently an infectious disease of high importance, which is said to be killing thousands of people in Japan and millions of people worldwide every year. In Japan, a person suspected of having tuberculosis infection must be hospitalized according to the Infectious Disease Law. A physician must immediately report to the authority when having diagnosed a patient with tuberculosis, and thus prompt responses are required.

*Mycobacterium tuberculosis* (human type of tuberculosis bacterium), *Mycobacterium bovis* (bovine type of tuberculosis bacterium), *Mycobacterium microti* (murine type of tuberculosis bacterium), and *Mycobacterium africanum* (African type of tuberculosis bacterium), which belong to a *Mycobacterium tuberculosis* complex, are known as acid-fast bacteria pathogenic to humans. *Mycobacterium avium*, *Mycobacterium kansasii*, *Mycobacterium marinum*, and the like are known as non-tuberculous mycobacteria.

Human infection with the *Mycobacterium tuberculosis* complex is mainly caused by *Mycobacterium tuberculosis* and, in some rare cases, by *Mycobacterium bovis*. Cases of infection with *Mycobacterium avium*, among the non-tuberculous mycobacteria, have been increased in recent years. Since both of these infections present similar clinical symptoms, the identification of a causative microbe is also important for determining courses of treatment.

Thus, the differential detection of tuberculosis infection or non-tuberculous mycobacterial infection is also important for reducing burdens on patients and appropriately conducting early treatment. In another aspect, the differential detection is also important for the purpose of preventing a third person from having secondary infection from the public health standpoint.

Heretofore, detection methods based on culture have been practiced as methods for detecting the *Mycobacterium tuberculosis* complex. Such culture methods are performed by inoculating a biological sample to be tested to either a liquid medium or a solid medium and detecting grown bacterial cells. The method using the liquid medium carries a high risk of secondary infection during operation and thus requires a highly safe facility and apparatus, though this method can shorten the culture period of the biological sample to be tested. The method using the solid medium requires a period as long as approximately 2 months to obtain detection results. The *Mycobacterium tuberculosis* complex must be cultured using a highly safe apparatus in a highly safe environment with great care being taken for preventing secondary infection.

As a method for identifying the *Mycobacterium tuberculosis* complex from the culture of the above-cultured biological sample, a convenient detection method is known which involves immunologically assaying a *Mycobacterium tuberculosis* complex-specific protein secreted into the medium.

Japanese Patent Laid-Open No. 11-108931 discloses a method for detecting the presence of a *Mycobacterium tuberculosis* complex, comprising: inoculating a biological sample collected from a tuberculosis patient, to a solid medium or a liquid medium; culturing the *Mycobacterium tuberculosis* complex for a few days to a few weeks; and then immunologically detecting a *Mycobacterium tuberculosis* complex-specific secretory protein MPB64 secreted into the medium. According to this reference, this method permits identification and detection of the *Mycobacterium tuberculosis* complex immediately after the culture and reduces the risk of secondary infection during operation, compared with conventional methods.

This method, however, involves culturing the *Mycobacterium tuberculosis* complex contained in the biological sample and using the resulting cultures as a sample. Hence, the method requires almost the same amount of time as the culture period until the *Mycobacterium tuberculosis* complex is detected and identified, and thus requires enormous labor and expense.

As described in Japanese Patent Laid-Open No. 11-108931, MPB64 is a *Mycobacterium tuberculosis* complex-specific secretory protein which is produced by *Mycobacterium bovis* BCG (*M. bovis* BCG) and extracellularly secreted. MPT64 is a *Mycobacterium tuberculosis* complex-specific secretory protein which is produced by *Mycobacterium tuberculosis* and extracellularly secreted.

MPB64 and MPT64 are known as identical substances. They may be individually referred to elsewhere in describing the inventions herein. They may also be conveniently designated as MPB64/MPT64 elsewhere herein.

Japanese Patent Laid-Open No. 2002-62299 states that the *Mycobacterium tuberculosis* complex-specific secretory protein MPT64 can be detected by immunological assay without culturing a *Mycobacterium tuberculosis* complex contained in a biological sample. This method involves treating a biological sample such as sputum and detecting MPT64 contained in the biological sample so that the presence of the *Mycobacterium tuberculosis* complex is detected.

However, even if the *Mycobacterium tuberculosis* complex is present in the biological sample, this method cannot detect the *Mycobacterium tuberculosis* complex unless MPB64 is extracellularly secreted by the *Mycobacterium tuberculosis* complex and contained in the biological sample. In addition, a small abundance of MPT64, albeit secreted, requires a large amount of the biological sample and complicates the operation. This poses increased burdens on test subjects and persons in charge of the tests. At the same time, infection with the *Mycobacterium tuberculosis* complex might be missed, resulting in public health problems.

International Publication No. WO 2009/084481 discloses a method for diagnosing tuberculosis infection more rapidly and more safely with higher accuracy than ever, comprising specifically detecting MPB64 in a biological sample using an antibody against a particular epitope in MPB64. According to this method, an applicable sample can be a cultures obtained by culturing a biological sample using a small amount of a liquid medium only for a time before bacterial cells of the *Mycobacterium tuberculosis* complex substantially start to grow.

This method, however, still demands a method for promoting the secretion of MPB64 from the bacterial cells before growth so that a larger amount of MPB64 accumulates in the medium.

CONVENTIONAL TECHNICAL DOCUMENTS

Patent Documents

Patent Document 1: Japanese Patent Laid-Open No. 11-108931
Patent Document 2: Japanese Patent Laid-Open No. 2002-62299
Patent Document 3: International Publication No. WO 2009/084481

SUMMARY OF INVENTION

Problems to be Solved by the Invention

As described above, the conventional methods require a long time for detecting a *Mycobacterium tuberculosis* complex and also require enormous labor and expense. For these reasons, definitive diagnosis and early start of treatment cannot be made for tuberculosis. Thus, there has been a demand for a more rapid method. Also, the direct detection from a biological sample cannot be performed if the biological sample contains no or a very small amount of MPB64/MPT64. As a result, infection with the *Mycobacterium tuberculosis* complex might be missed. Thus, there has been a need for a more reliable detection method. An object of the present invention is to solve these problems by providing a convenient, rapid, and more reliable method for detecting a *Mycobacterium tuberculosis* complex.

Means for Solving the Problems

The present inventors have conducted diligent studies to solve the above problems and consequently found that the problems can be solved by heat-treating a biological sample containing a *Mycobacterium tuberculosis* complex so as to extracellularly secrete a *Mycobacterium tuberculosis* complex-specific secretory protein such as MPB64 and detecting the thus-secreted protein, and as a result, the present invention has been completed.

According to one aspect, the present invention provides a method for detecting a *Mycobacterium tuberculosis* complex, comprising subjecting a *Mycobacterium tuberculosis* complex-specific protein to an immunological assay, wherein said protein is extracellularly secreted by subjecting a biological sample containing the *Mycobacterium tuberculosis* complex to a heat-treatment. According to another aspect, the present invention also provides a kit for detection of a *Mycobacterium tuberculosis* complex, comprising at least a treatment container in which a biological sample containing the *Mycobacterium tuberculosis* complex is subjected to a heat-treatment, and an immunological assay apparatus for detecting a *Mycobacterium tuberculosis* complex-specific secretory protein secreted by the heat-treatment, as a kit for detection of a *Mycobacterium tuberculosis* complex for the purpose of carrying out the above method. The kit may further comprise a sample treating agent and/or a solvent. The detection method and the kit of the present invention are capable of rapidly and conveniently detecting the *Mycobacterium tuberculosis* complex. According to a further aspect, the present invention also provides a method for extracellularly secreting a *Mycobacterium tuberculosis* complex-specific protein, comprising subjecting a biological sample containing the *Mycobacterium tuberculosis* complex to a heat-treatment.

DESCRIPTION OF EMBODIMENTS

Figure 1:
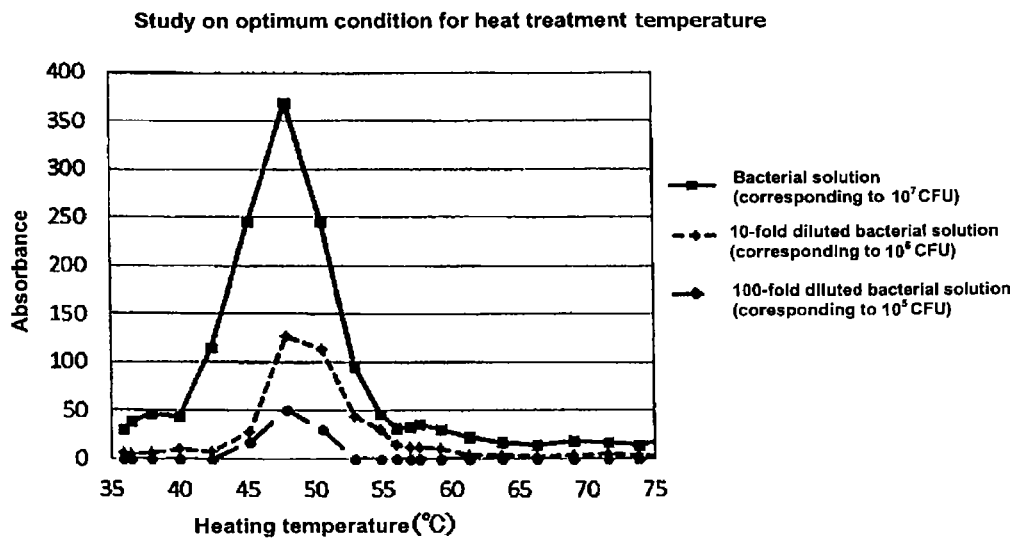
FIG. 1 is a graph showing the relationship between the heat-treatment temperature and the effect of promoting extracellular MPB64 secretion, when bacterial cells of a *M. bovis* BCG Tokyo strain were used.

The biological sample used in the present invention is not particularly limited as long as the biological sample may contain a *Mycobacterium tuberculosis* complex. Examples of the biological sample include sputum, pleural effusion, bronchial secretion, gastric juice, blood, spinal fluid, urine, and feces. Preferably, sputum is used because of its high bacterial concentration. Alternatively, bronchial lavage fluid collected during respiratory examination, a tissue collected from the bronchus or the lung, or the like may be used as the biological sample. These biological samples may each be used alone or may be used as a mixture of two or more thereof.

The heat-treatment of the biological sample is preferably carried out by placing the biological sample in a hermetically sealable container and then subjecting the container as a whole to a heat-treatment because the biological sample to be treated contains a highly infectious *Mycobacterium tuberculosis* complex. The heat-treatment operation is preferably performed within a safety cabinet from the viewpoint of securing the safety of an operator. The container for use in the heat-treatment is not particularly limited as long as the container can maintain its hermetically sealed state and can resist a predetermined heating temperature. The container can be appropriately selected according to the biological sample to be treated. The container may be equipped, at its opening, with a dropper nozzle with a filter so as to facilitate the discharge of the thus-treated biological sample from the container, for immunological assay. Use of the dropper nozzle with a filter is preferred because the dropper nozzle with a filter can remove solid matter such as denatured components contained in the treated biological sample and further, can conveniently put drops of the resulting biological sample to an immunological assay apparatus.

The biological sample may be subjected to a treatment such as lysis with a sample treating agent according to its properties before the heat-treatment. For example, when sputum is used as the sample, it may be lysed with an alkaline substance, a reducing substance, a protease, a sugar, a surfactant, a protein denaturant, or the like, which reduces the viscosity of sputum, in order to improve the efficiency of the heat-treatment. Particularly, a treatment using sodium hydroxide as an alkaline substance and N-acetyl-L-cysteine as a reducing substance in combination is convenient and is preferably used.

According to another embodiment, the biological sample may be dispersed or dissolved in a solvent and then subjected to a heat-treatment. The solvent can be, for example, any solvent that can keep the *Mycobacterium tuberculosis* complex contained in the biological sample alive. A buffer solution such as phosphate-buffered saline or a liquid medium for use in acid-fast bacterium isolation culture such as Middlebrook 7H9 can be used. Particularly, a liquid medium is preferably used because the protein needs to be extracellularly secreted by the heat-treatment without impairing the activity of the *Mycobacterium tuberculosis* complex and because the thus-treated sample can be subjected directly to an immunological assay. Alternatively, the biological sample lysed with the sample treating agent may be redispersed in the solvent.

The heating temperature for the biological sample can be any temperature at which the protein can be extracellularly secreted into the biological sample or the solvent by the *Mycobacterium tuberculosis* complex, and is preferably in the range of 40° C. to 60° C., more preferably in the range of 40° C. to 55° C. Particularly, the temperature that effectively promotes the secretion is in the range of 45° C. to 50° C.

The treatment time for the biological sample can be a time that is sufficient to extracellularly secrete a detectable amount of the *Mycobacterium tuberculosis* complex-specific secretory protein while the treatment temperature is kept within the above range. The treatment time is preferably 15 minutes or longer, more preferably 15 minutes or longer and 2.5 hours or shorter, further preferably 15 minutes or longer and 1.5 hours or shorter, most preferably 30 minutes or longer and 1 hour or shorter.

The sample thus heat-treated may be subjected to the inactivation treatment of the *Mycobacterium tuberculosis* complex merely by raising the heating temperature. The temperature for the inactivation treatment of the *Mycobacterium tuberculosis* complex is not particularly limited but is preferably 100° C. The inactivation of the *Mycobacterium tuberculosis* complex contained in the sample allows immunological assay to be conducted safely without the risk of secondary infection.

The heating apparatus for use in the heat-treatment is not particularly limited as long as the apparatus is capable of keeping the temperature constant. A thermostat bath, a heater block, an incubator, or the like can be used. A small heating apparatus is particularly preferred because all the procedures for detecting the *Mycobacterium tuberculosis* complex can be completed within a safety cabinet.

According to the present invention, the *Mycobacterium tuberculosis* complex-specific protein can be extracellularly secreted by the heat-treatment of the biological sample. The presence of the *Mycobacterium tuberculosis* complex can therefore be easily detected by immunological assay or the like using the biological sample thus treated.

In the present invention, the *Mycobacterium tuberculosis* complex-specific protein to be extracellularly secreted is not particularly limited as long as the protein is extracellularly secreted. Examples of the protein that is extracellularly secreted by the *Mycobacterium tuberculosis* complex include many proteins such as MPB64 (i.e., MPT64), MPB70, ESAT-6, and CFP-10. Of these proteins, a protein that is extracellularly secreted in a large amount in a short time is preferred as a protein used as an index for indicating the presence of the *Mycobacterium tuberculosis* complex in the immunological assay used in the present invention. For example, MPB64, i.e., MPT64, is extracellularly secreted or released in a large amount by the heat-treatment of the biological sample according to the present invention without culture, i.e., before the bacterial cells start to grow. From such a viewpoint, MPB64, i.e., MPT64 is preferably used as a target for the detection of the presence of the *Mycobacterium tuberculosis* complex. The extracellularly secreted MPB64, i.e., MPT64 can be immunologically assayed so as to determine the presence or absence of the *Mycobacterium tuberculosis* complex.

In the detection method of the present invention, the immunological assay is not particularly limited and is preferably a sandwich immunoassay using a first antibody and a second antibody against the *Mycobacterium tuberculosis* complex-specific secretory protein, particularly, enzyme-linked immunosorbent assay (ELISA) or immunochromatographic assay. The first antibody and the second antibody may be the same or may be different from each other as long as they permit detection of the *Mycobacterium tuberculosis* complex-specific secretory protein.

This immunological assay can be any method capable of immunologically detecting MPB64 extracellularly secreted by the heat-treatment of the biological sample and is preferably immunochromatographic assay, particularly preferably immunochromatographic assay using an anti-MPB64 monoclonal antibody. The immunochromatographic assay for MPB64 detection can be easily conducted in accordance with the method described in Japanese Patent Laid-Open No. 11-108931. In addition, Capilia® TB (manufactured by TAUNS Laboratories, Inc.), a commercially available immunochromatographic assay apparatus for detection of MPB64, i.e., MPT64, can be used.

EXAMPLES

The present invention will be described further specifically by way of Examples below. However, the present invention is not intended to be limited by these Examples.

Reference Example 1

Preparation of a Bacterial Solution to be Tested 4.7 g of Middlebrook 7H9 broth base (manufactured by Difco Laboratories Inc.) was dissolved in 900 ml of distilled water containing 0.5 g of Tween 80. The solution was high-pressure sterilized in an autoclave at 121° C. for 10 minutes. After cooling, 100 ml of ADC Enrichment (albumin-dextrose-catalase) was aseptically added thereto to prepare a Middlebrook 7H9 liquid medium.

A *M. bovis* BCG Tokyo strain (hereinafter, referred to as a BCG strain) was inoculated to the above-prepared liquid medium, and cultured according to a standard method. The culture was continued until turbidity corresponding to McFarland standards No. 1 was obtained. The resulting bacterial solution was centrifuged to recover bacterial cells. The recovered bacterial cells were resuspended by the addition of the above-mentioned Middlebrook 7H9 liquid medium and then further centrifuged to recover bacterial cells. This operation was repeated three times. The bacterial cells were washed to remove *Mycobacterium tuberculosis* complex secretory proteins attached to the bacterial cells. 100 μL of the supernatant after the washing operation was applied to Capilia® TB (manufactured by TAUNS Laboratories, Inc.), an immunochromatographic assay apparatus for MPB64 detection. As a result, this product exhibited negativity to confirm that secreted MPB64 was absent in the supernatant.

Example 1

Study on Optimum Condition for Heat-Treatment Temperature

The optical density of the bacterial solution having the turbidity corresponding to McFarland standards No. 1, prepared in Reference Example 1, was adjusted to O.D. 0.1 at an absorbance of 530 nm to prepare a bacterial solution for testing (bacterial count: corresponding to $10^7$ CFU). The bacterial solution for testing was further diluted with a liquid medium to prepare a 10-fold diluted bacterial solution (bacterial count: corresponding to $10^6$ CFU) and a 100-fold diluted bacterial solution (bacterial count: corresponding to $10^5$ CFU). 200 µl of each prepared bacterial solution was dispensed to each plastic tube (a tube for nucleic acid amplification) and heat-treated using a temperature-controllable heat block for a nucleic acid amplification apparatus. The heating temperature was set to temperatures differing by 5° C. from 35° C. to 75° C. The heat-treatment was carried out for 30 minutes. Samples heat-treated at an ordinary culture temperature of 35° C. were used as controls. A 100 µl aliquot was collected from each sample thus treated, and applied to Capilia® TB (manufactured by TAUNS Laboratories, Inc.) in the same way as in Reference Example 1 to detect the presence of MPB64. The absorbance of the reading area was measured using Immno Chromato-Reader (manufactured by Otsuka Electronics Co., Ltd.).

The results are shown in FIG. 1. In FIG. 1, the ordinate represents the measurement value of color intensity (absorbance) in Capilia® TB (manufactured by TAUNS Laboratories, Inc.), and the abscissa represents the heating temperature. The relationship between the absorbance and the treatment temperature is indicated by solid line for the results about the bacterial solution for testing (bacterial count: corresponding to $10^7$ CFU), by broken line for the results about the 10-fold diluted bacterial solution (bacterial count: corresponding to $10^6$ CFU), and by long broken line for the results about the 100-fold diluted bacterial solution (bacterial count: corresponding to $10^5$ CFU).

As seen from the results, all of the tested samples exhibited a rise in absorbance at 40° C. to 60° C., particularly, a marked rise at 45° C. to 50° C. This indicates that the heat-treatment of the bacterial cells promoted their extracellular MPB64 secretion. The controls treated under an ordinary culture condition of 35° C. exhibited no rise in absorbance, demonstrating that just keeping a sample at room temperature or under conditions equivalent thereto does not cause MPB64 to be extracellularly secreted. On the other hand, no rise in absorbance was confirmed in a temperature range higher than the temperature range from 40° C. to 60° C. where the secretion of MPB64 was confirmed. This showed that MPB64 is not secreted in a temperature range equal to or higher than 60° C.

Accordingly, from these results, the heat-treatment of a bacterial sample at 40° C. to 60° C., particularly, at 45° C. to 50° C. was confirmed to markedly promote extracellular MPB64 secretion and markedly increase the detection rate of immunological assay.

Example 2

Study on Optimum Condition for Heat-Treatment Temperature

The optical density of the bacterial solution having the turbidity corresponding to McFarland standards No. 1, prepared in Reference Example 1, was adjusted to O.D. 0.1 at an absorbance of 530 nm to prepare a bacterial solution for testing (bacterial count: corresponding to $10^7$ CFU). 200 µl of the prepared bacterial solution was dispensed to each plastic tube (a tube for nucleic acid amplification) and heat-treated using a temperature-controllable heat block for a nucleic acid amplification apparatus. The heating temperature was set to 35° C., 13 temperatures differing by 2° C. from 40° C. to 64° C., and 2 temperatures of 70° C. and 80° C. as a high temperature range. The heat-treatment was carried out for 60 minutes. Samples heated-treated at an ordinary culture temperature of 35° C. were used as controls. A 100 µl aliquot was collected from each sample thus treated, and applied to Capilia® TB (manufactured by TAUNS Laboratories, Inc.) in the same way as in Reference Example 1 to detect the presence of MPB64. Evaluation was conducted by the visual observation of the color intensity of a labeling substance accumulated in the reading area. The color intensity was visually evaluated as the degree of magenta color on the basis of 5 grades: − (not colored), ± (weakly colored), + (distinctly colored), ++ (more distinctly colored), and +++ (markedly colored). The evaluation results are shown in Table 1.

TABLE 1

| Treatment temperature | Evaluation |
| --- | --- |
| 35° C. (control) | − |
| 40° C. | ± |
| 42° C. | + |
| 44° C. | + |
| 46° C. | ++ |
| 48° C. | +++ |
| 50° C. | +++ |
| 52° C. | ++ |
| 54° C. | + |
| 56° C. | + |
| 58° C. | + |
| 60° C. | ± |
| 62° C. | − |
| 64° C. | − |
| 70° C. | − |
| 80° C. | − |

As seen from the results of Table 1, a rise in color intensity was exhibited at 40° C. to 60° C., and particularly, a marked rise was confirmed at 44° C. to 52° C. This indicates that the heat-treatment of the bacterial cells promoted their extracellular MPB64 secretion, as in Example 1. The controls treated under an ordinary culture condition of 35° C. exhibited no rise in absorbance, demonstrating that just keeping a sample at room temperature or under conditions equivalent thereto does not cause MPB64 to be extracellularly secreted. On the other hand, no rise in absorbance was confirmed at the temperatures equal to or higher than 62° C. or in the high temperature range of 70° C. and 80° C. This showed that MPB64 is not secreted in a temperature range equal to or higher than 60° C.

Accordingly, from these results, the heat-treatment of a bacterial sample at 40° C. to 60° C., particularly, at 45° C. to 50° C. was confirmed to markedly promote extracellular MPB64 secretion and markedly increase the detection rate of immunological assay.

Example 3

Study on Optimum Condition for Heat Treatment Time

The optical density of the bacterial solution having the turbidity corresponding to McFarland standards No. 1, prepared in Reference Example 1, was adjusted to O.D. 0.1 at an absorbance of 530 nm to prepare a bacterial solution for testing (bacterial count: corresponding to $10^7$ CFU). 200 µl of the prepared bacterial solution was dispensed to each plastic tube and heat-treated using a temperature-controllable heat block for a nucleic acid amplification apparatus. The heat operation was carried out with the heating temperature set to temperatures differing by 5° C. from 35° C. to 75° C. The treatment time was set to 0 minutes, 15 minutes, 30 minutes, and 60 minutes. A 100 µl aliquot was collected from each sample thus treated, and applied to Capilia® TB (manufactured by TAUNS Laboratories, Inc.) in the same way as in Example 1. The absorbance of the reading area was measured using Immno Chromato-Reader (manufactured by Otsuka Electronics Co., Ltd.).

Figure 2:
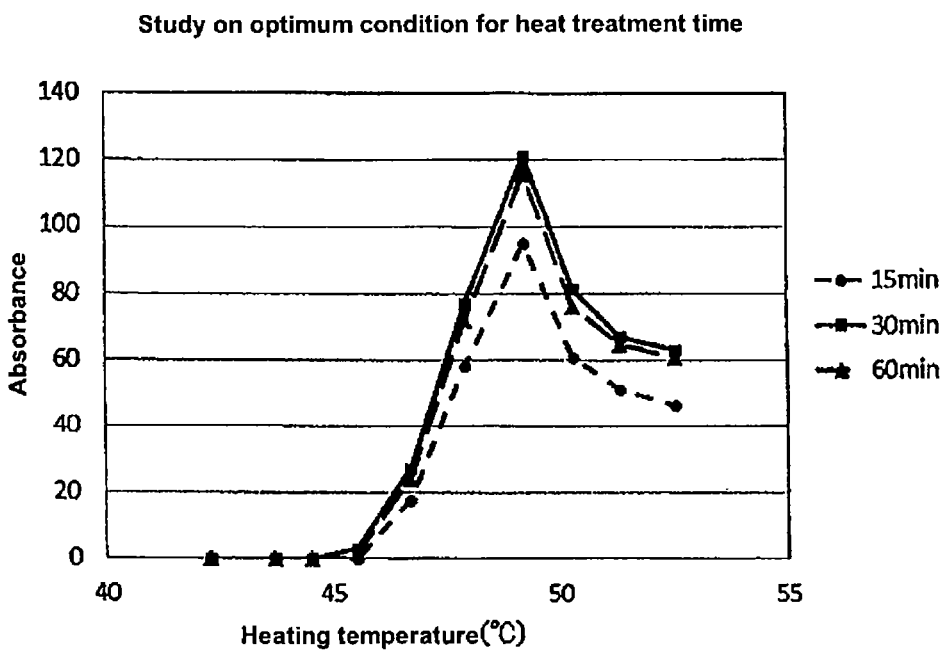
FIG. 2 is a graph showing the relationship between the heat treatment time and the effect of promoting extracellular MPB64 secretion, when bacterial cells of a *M. bovis* BCG Tokyo strain were used.

The results are shown in FIG. 2. In FIG. 2, the ordinate represents the measurement value of color intensity (absorbance) in Capilia® TB (manufactured by TAUNS Laboratories, Inc.), and the abscissa represents the heating temperature. The relationship between the absorbance and the treatment temperature is indicated by broken line for the results about the samples treated for the treatment time of 15 minutes, by solid line for the results about the samples treated for the treatment time of 30 minutes, and by long broken line for the results about the samples treated for the treatment time of 60 minutes.

As seen from the results, all of the samples treated for the treatment time of 15 minutes, 30 minutes, and 60 minutes exhibited a marked rise in absorbance at the temperature of 45° C. to 50° C. No difference was seen among the treatment times. Even the samples treated for the heating time of 60 minutes were not confirmed to largely differ from the other samples. Accordingly, the heat treatment time of at least 15 minutes was confirmed to have the effect of promoting extracellular MPB64 secretion.

Example 4

Study on Optimum Condition for Heat Treatment Time

The optical density of the bacterial solution having the turbidity corresponding to McFarland standards No. 1, prepared in Reference Example 1, was adjusted to O.D. 0.01 at an absorbance of 530 nm to prepare a bacterial solution for testing (bacterial count: corresponding to $10^6$ CFU). 200 µl of the prepared bacterial solution was dispensed to each plastic tube and heat-treated at 50° C. using a temperature-controllable heat block for a nucleic acid amplification apparatus. The heat-treatment was carried out with the treatment time set to 0 minutes, 15 minutes, 30 minutes, 45 minutes, 60 minutes, 75 minutes, 120 minutes, and 150 minutes. As a control, the same bacterial solution to be tested as above was left at room temperature without heat-treatment. A 100 µl aliquot was collected from each sample thus treated, and applied to Capilia® TB (manufactured by TAUNS Laboratories, Inc.) in the same way as in Example 1. The color intensity of an accumulated labeling substance was visually observed. The color intensity was visually evaluated as the degree of magenta color on the basis of 5 grades: − (not colored), ± (weakly colored), + (distinctly colored), ++ (more distinctly colored), and +++ (markedly colored). The evaluation results are shown in Table 2.

TABLE 2

|  | 50° C. heat-treatment Evaluation | Control (no heat-treatment) Evaluation |
|---|---|---|
| 0 min | − | − |
| 15 min | + | − |
| 30 min | + | − |
| 45 min | ++ | − |
| 60 min | +++ | − |
| 75 min | +++ | − |
| 120 min | +++ | − |
| 150 min | +++ | − |

As seen from the results of Table 2, the non-heat-treated control sample and the sample treated for the heating time of 0 minutes were confirmed to develop no color in the reading area. The heat-treatment for 15 minutes was confirmed to produce color derived from extracellular MPB64 secretion. The sample heat-treated for 60 minutes was confirmed to develop marked color. The samples heat-treated for up to 150 minutes exhibited no further rise in color intensity and were confirmed to develop marked color at the same level as that of the sample heat-treated for 60 minutes. From these results, heat-treatment for at least 15 minutes was confirmed to have the effect of promoting extracellular MPB64 secretion, which peaked at 60 minutes.

Example 5

Study on Solvent

The bacterial solution having the turbidity corresponding to McFarland standards No. 1, prepared in Reference Example 1, was prepared into bacterial solutions having a bacterial count corresponding to $10^7$ CFU, $10^6$ CFU, or $10^5$ CFU using a Tween 80-containing phosphate buffer solution or a Middlebrook 7H9 liquid medium as a solvent for biological sample treatment to prepare test samples. 200 µl of each test sample was dispensed to each plastic tube. Then, the sample was heat-treated at 50° C. for 30 minutes in a heat block. Then, a 100 µl aliquot was collected from the sample thus treated, and applied to Capilia® TB (manufactured by TAUNS Laboratories, Inc.) in the same way as in Example 1, followed by evaluation. The evaluation was conducted by the visual observation of the color intensity of a labeling substance accumulated in the reading area. The color intensity was visually evaluated as the degree of magenta color on the basis of 5 grades: − (not colored), ± (weakly colored), + (distinctly colored), ++ (more distinctly colored), and +++ (markedly colored). The evaluation results are shown in Table 3.

TABLE 3

|  |  | Solvent | |
|---|---|---|---|
|  |  | Tween 80-containing phosphate buffer solution | Middlebrook 7H9 liquid medium |
| Test sample (bacterial concentration) | Corresponding to $10^5$ CFU | + | ++ |
|  | Corresponding to $10^6$ CFU | ++ | +++ |
|  | Corresponding to $10^7$ CFU | +++ | +++ |

As is evident from the results of Table 3, extracellularly secreted MPB64 can be detected in both cases where the Tween 80-containing phosphate buffer solution is used as a solvent and where the Middlebrook 7H9 liquid medium is used as a solvent. Thus, no difference in immunological assay was confirmed among variations in the composition of a solvent.

Example 6

Detection from Sputum Sample

The bacterial solution having the turbidity corresponding to McFarland standards No. 1, prepared in Reference Example 1, was added to sputum that had been confirmed to be negative for tuberculosis infection to prepare a pseudo-positive sputum sample having a bacterial count corresponding to $10^7$ CFU. This sample was dispensed to plastic tubes. To each of these sputum samples, N-acetyl-L-cysteine and an aqueous sodium hydroxide solution were added in equal amounts, and the mixture was left standing at room temperature for 15 minutes to lyse the sample. Then, the sample was heat-treated at 50° C. for 30 minutes using a heat block. Then, a 100 μl aliquot was collected from the sample thus treated, and applied to Capilia® TB (manufactured by TAUNS Laboratories, Inc.) in the same way as in Example 1, followed by evaluation. Control sputum samples were treated in the same way as above except that they were left standing at room temperature for 30 minutes without the heat-treatment, followed by evaluation. The evaluation was conducted by the visual observation of the color intensity of a labeling substance accumulated in the reading area. The color intensity was visually evaluated as the degree of magenta color on the basis of 5 grades: − (not colored), ± (weakly colored), + (distinctly colored), ++ (more distinctly colored), and +++ (markedly colored). The evaluation results are shown in Table 4.

TABLE 4

| | No heat-treatment | 50° C. heat-treatment |
|---|---|---|
| Sample <1> | − | + |
| Sample <2> | − | + |
| Sample <3> | − to ± | ++ |
| Sample <4> | − | + |

As a result, the heat-treated samples were confirmed to develop evident color in the reading area, demonstrating the presence of MPB64 in the samples. By contrast, the control samples evidently differed from the heat-treated samples, though some samples exhibited slight color in the reading area. Accordingly, the heat-treatment was confirmed to promote MPB64 secretion even in a sputum sample, demonstrating that the *Mycobacterium tuberculosis* complex can be detected rapidly and conveniently from a biological sample.

INDUSTRIAL APPLICABILITY

The present invention provides a method for detecting a *Mycobacterium tuberculosis* complex which can be conveniently and rapidly performed directly from a biological sample containing the *Mycobacterium tuberculosis* complex without culture operation by heat-treating the biological sample at a predetermined temperature and immunologically assaying a *Mycobacterium tuberculosis* complex-specific secretory protein thus extracellularly secreted, and also provides a kit directed thereto. The present invention is useful not only for the detection of the *Mycobacterium tuberculosis* complex but for the appropriate diagnosis and treatment of tuberculosis.

The invention claimed is:

1. A method for detecting the presence of a *Mycobacterium tuberculosis* complex-specific protein in a heat-treated biological sample, the method comprising subjecting a heat-treated biological sample to an immunological assay for the presence of the *Mycobacterium tuberculosis* complex-specific protein, wherein the *Mycobacterium tuberculosis* complex-specific protein is MPB64/MPT64, wherein the heat-treated biological sample to be immunologically assayed is obtained by subjecting a biological sample that may contain *Mycobacterium tuberculosis* complex to a heat-treatment carried out at 45° C. to 60° C. for a time sufficient to promote extracellular secretion of the *Mycobacterium tuberculosis* complex-specific protein MPB64/MPT64, and wherein the biological sample is lysed with a sample treating agent before being subjected to the heat-treatment.

2. A method according to claim 1, wherein the heat-treatment of the biological sample is carried out at 45° C. to 55° C.

3. A method according to claim 2, wherein the heat-treatment of the biological sample is carried out at 45° C. to 50° C.

4. A method according to claim 1, wherein the biological sample is selected from the group consisting of sputum, bronchial secretion, pleural effusion, gastric juice, blood, spinal fluid, urine, feces, bronchial lavage fluid, and a tissue collected from the bronchus or the lung.

5. A method according to claim 4, wherein the biological sample is sputum.

6. A method for according to claim 1, wherein the biological sample lysed with a sample treating agent is dispersed or dissolved in a solvent before being subjected to the heat-treatment.

7. A method according to claim 1, wherein the immunological assay is a sandwich immunoassay using a first antibody and a second antibody against the *Mycobacterium tuberculosis* complex-specific protein.

8. A method according to claim 7, wherein the immunological assay is an immunochromatographic assay.

9. A method according to claim 7, wherein the immunological assay is ELISA.

10. A method for extracellularly secreting a *Mycobacterium tuberculosis* complex-specific protein MPB64/MPT64, comprising subjecting a biological sample containing a *Mycobacterium tuberculosis* complex that secretes a *Mycobacterium tuberculosis* complex-specific protein MPB64/MPT64 to a heat-treatment that is carried out at 45° C. to 60° C. for 15 to 60 minutes whereby said *Mycobacterium tuberculosis* complex-specific protein MPB64/MPT64 is extracellularly secreted, wherein the biological sample is lysed with a sample treating agent before being subjected to the heat-treatment.

11. A method according to claim 1, said method comprising:

subjecting the lysed biological sample to the heat-treatment at 45° C. to 60° C. for 15 to 60 minutes to promote extracellular secretion of the *Mycobacterium tuberculosis* complex-specific protein MPB64/MPT64;

preparing the heat-treated sample for immunological assaying; and subjecting the heat-treated sample to the immunological assay for the presence of *Mycobacterium tuberculosis* complex-specific protein MPB64/MPT64.

12. A method for detecting the presence of a *Mycobacterium tuberculosis* complex-specific protein in a heat-treated biological sample, the method comprising
subjecting a heat-treated biological sample to an immunological assay for the presence of the *Mycobacterium tuberculosis* complex-specific protein, wherein the *Mycobacterium tuberculosis* complex-specific protein is MPB64/MPT64,
wherein the heat-treated biological sample to be immunologically assayed for the presence of the *Mycobacterium tuberculosis* complex-specific protein is obtained from a biological sample, which was obtained from a subject, that has been subjected to a heat-treatment carried out at 45° C. to 60° C. for a time sufficient for promoting *Mycobacterium tuberculosis* complex that may be present in the biological sample to extracellularly secrete a detectable amount of the *Mycobacterium tuberculosis* complex-specific protein MPB64/MPT64, and wherein said biological sample has been lysed with a sample treating agent before being subjected to the heat-treatment.

13. A method for detecting for the presence of *Mycobacterium tuberculosis* complex-specific protein MPB64/MPT64 in a heat-treated biological sample, the method comprising:
subjecting an aliquot of a heat-treated biological sample to an immunological assay to detect for the presence of *Mycobacterium tuberculosis* complex-specific protein MPB64/MPT64,
wherein the aliquot of the heat-treated biological sample to be immunologically assayed for the presence of said *Mycobacterium tuberculosis* complex-specific protein MPB64/MPT64 is obtained by
collecting a biological sample from a subject, wherein said biological sample may contain *Mycobacterium tuberculosis* complex and said biological sample is selected from the group consisting of sputum, bronchial secretion, pleural effusion, gastric juice, blood, spinal fluid, urine, feces, bronchial lavage fluid, and a tissue collected from the bronchus or the lung,
lysing the biological sample with a sample treating agent,
subjecting the lysed biological sample to a heat-treatment carried out at 45° C. to 60° C. for a time sufficient for inducing *Mycobacterium tuberculosis* complex that may be present in the biological sample to extracellularly secrete *Mycobacterium tuberculosis* complex-specific protein MPB64/MPT64, and
collecting and preparing the aliquot from the heat-treated biological sample.

14. A method for detecting the presence of *Mycobacterium tuberculosis* complex-specific protein MPB64/MPT64 in a biological sample, the method comprising:
collecting a biological sample from a subject, wherein said biological sample may contain *Mycobacterium tuberculosis* complex and said biological sample is selected from the group consisting of sputum, bronchial secretion, pleural effusion, gastric juice, blood, spinal fluid, urine, feces, bronchial lavage fluid, and a tissue collected from the bronchus or the lung,
lysing the biological sample with a sample treating agent,
subjecting the lysed biological sample to a heat-treatment carried out at 45° C. to 60° C. for 15 to 60 minutes to induce *Mycobacterium tuberculosis* complex that may be present in the biological sample to extracellularly secrete the *Mycobacterium tuberculosis* complex-specific protein,
collecting and preparing an aliquot from the heat-treated biological sample for immunological assay, and
subjecting the aliquot of the heat-treated biological sample to an immunological assay to detect for the presence of the *Mycobacterium tuberculosis* complex-specific protein MPB64/MPT64.

* * * * *